US00PP11543P

United States Patent [19]

Olesen et al.

[11] Patent Number: Plant 11,543

[45] Date of Patent: Oct. 3, 2000

[54] MINIATURE ROSE PLANT NAMED 'POULRAC'

[75] Inventors: L. Pernille Olesen; Mogens N. Olesen, both of Fredensborg, Denmark

[73] Assignee: Poulsen Roser ApS, Fedensborg, Denmark

[21] Appl. No.: 09/122,188

[22] Filed: Jul. 23, 1998

[51] Int. Cl.[7] ..... A01H 5/00

[52] U.S. Cl. ..... Plt./122

[58] Field of Search ..... Plt./121, 122

[56] References Cited

PUBLICATIONS

UPOV–ROM, Feb. 2, 1999, Plant Variety Database, GTI Jouve Retrieval Software, Citation for 'POULrac'.

*Primary Examiner*—Howard J. Locker

[57] ABSTRACT

A new miniature pot rose plant which has abundant, non-fading, dark red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between 'POULpol' and an unnamed seedling. The two parents were crossed and the resulting seeds were planted in a controlled environment. The new variety is named 'POULrac'.

The new rose may be distinguished from its seed parent, 'POULpol', by the following combination of characteristics:

1. 'POULrac' is a miniature rose variety with dark red blooms whereas the seed parent 'POULpol' is a miniature rose with pink blooms.

2. The flowers of 'POULrac' are larger in diameter and more double than 'POULpol'.

3. 'POULrac' has more flowers than 'POULpol'.

4. The flowers of 'POULrac' have greater lastingness.

The new variety may be distingushed from its pollen parent, an 'unnamed seedling' created by the same inventors, by the following combination of characteristics:

1. 'POULrac' has dark red blooms, while the pollen parent has pink blooms.

2. The unnamed seedling is an offspring of 'Maria Mathilda' (a white floribunda) and 'POULstar', a white miniature rose variety by the same inventors described in U.S. Plant Pat. No. 9,016 granted on Dec. 20, 1994.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULrac' was selected by the inventors as a single plant from the progeny of the hybridization during June, 1995.

Asexual reproduction of 'POULrac' by cuttings and traditional budding was first done by L. Pernille and Mogens N. Olesen in their nursery in Fredensborg, Denmark in August, 1996. This initial and subsequent propagations conducted in controlled environments have demonstrated that the characteristics of 'POULrac' are true to type and are transmitted from one generation to the next.

BRIEF DESCRIPTION OF THE DRAWING

The accompanying color illustration shows as true as is reasonably possible to obtain in color photographs of this type, the typical characteristics of the bud, flowers, leaves, stems, and a plant of 'POULrac'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a detailed description of 'POULrac', as observed in its growth in glasshouses in Fredensborg, Denmark and Half Moon Bay, Calif. and in field nursery in Jackson County, Oreg. Color references are made using The Royal Horticultural Society (London, England) Colour Chart, 1995, except where common terms of color are used.

For a comparison, the nearest existing rose variety is 'POULhappy', a patented variety by the same inventors described and illustrated in U.S. Plant Pat. No. 9,483 and issued on Mar. 26, 1996. Chart 1 details several physical characteristics of 'POULrac' and 'POULhappy'.

CHART 1

| | 'POULrac' | 'POULhappy' |
|---|---|---|
| Bud color at ¼open | Red Group 53A to Red-Purple Group 60B | Red Group 46B |
| Upper petal surface, open bloom | Between Red Group 46A and Red-Purple Group 60B | Red Group 46B |

CHART 1-continued

| | 'POULrac' | 'POULhappy' |
|---|---|---|
| Reverse petal surface, open bloom | Red Group 46A | Red Group 46B |

Parents: 'POULpol'×'unnamed seedling'.
Classification:
*Botanical.*—*Rosa hybrida.*
*Commercial.*—Miniature.

FLOWER AND FLOWER BUD

Blooming habit: Continuous.
Flower bud:
*Size.*—Upon opening, 16 mm–18 mm in length.
*Bud form.*—Ovoid to rounded.
*Bud color.*—Red Group 53A to Red-Purple Group 60B at ¼ opening.
*Sepals.*—Green Group 143A. Weak foliaceous appendages on three of the five sepals. Surfaces of sepals lightly pubescent. Stipitate glands present.
*Peduncle.*—Surface: With stiff stipitate glands. Length: 25–40 mm average length. Color: Green Group 143A. Strength: Upright.
*Receptacle.*—Surface: Smooth. Shape: Funnel-shaped. Size: Small. 5 mm×5 mm. Color: Green Group 143A.
*Borne.*—Generally with 3–7 buds per flowering stem.
Flower bloom:
*Size.*—Medium for a 10 cm pot rose. Average diameter is 40–45 mm when open.
*Form.*—Upon opening, form of upper part of flower is flat to cupped. Shape of lower part of bloom is a flattened convex. Completely open, upper part of bloom is cup-shaped to flat. Outermost petals reflex slightly.
*Petalage.*—Double. Average range: 35–40 under normal conditions.
*Color.*—Upon opening, upper surface of the petals is between Red Group 46A and Red-Purple Group 60B. Upon opening, the reverse surface is Red Group 46A. After opening, the upper surface is Red Group 46A. After opening, the reverse surface is Red Group 46A. A petal spot, Green-White Group 157D, exists on the inner and outer sides of the bases of the petals.
*General tonality.*—No change in the general tonality at the end of the first day. At the end of the third day, there is a slight change to Red Group 46B.
*Petal reflex.*—Petals reflex backwards slightly.
*Petal edge.*—Generally with point in center.
*Petaloids.*—Limited. 1–5 per bloom.
*Fragrance.*—None.
*Duration.*—As a pot plant, flowers last from 16 to 18 days. As a cut flower 8 to 12 days.
Petals:
*Texture.*—Thin.
*Arrangement.*—Regular.
Reproductive organs:
*Pollen.*—Color: Yellow-Orange Group 14B. Abundance: Above average.
*Anthers.*—Size: Medium. Color: Yellow-Orange Group 14B. Abundance: Above average.
*Filaments.*—Color: Yellow-Green Group 145D.
*Stigmas.*—Slightly superior in location to anthers. Color: Yellow-Green Group 145D with intonations of Red-Purple Group 58A.
*Styles.*—Color: Yellow-Green Group 145D.

PLANT

Plant growth: Vigorous, compact, upright to bushy. When grown as a 10 cm pot plant, the average height of the plant itself is 16 to 18 cm and the average width is 16 to 18 cm. When grown as a nursery plant on its own roots the average plant height is 25–35 cm and the average plant width is 20–25 cm.
Stems:
*Color.*—Young wood: Yellow-Green Group 144A. Older wood: Yellow-Green Group 143B.
*Thorns.*—Incidence: Per each 10 cm of stem, there are 8–10 thorns that are 5–7 mm in length. There are few small thorns. Color: Green-White Group 157A. Some thorns with intonations of Red Group 56B. Older thorns Greyed-Orange Group 164D. Shape: Linear.
*Bark.*—Young wood: Smooth. Older wood: Smooth.
Plant foliage: Normal number of leaflets on normal leaves in middle of the stem: 5 leaflets. Some lower leaves with 7 leaflets.
*Leaf size.*—Medium.
*Abundance.*—Average.
*Color.*—Upper Leaf Surface: Green Group 137A. Lower Leaf Surface: Green Group 138A–138B. Juvenile foliage: Green Group 143A, with limited anthocyanin coloration of Greyed-Red Group 179A on underside and margins of leaflets.
Plant leaves and leaflets:
*Stipules.*—Present. Stipitate glands present on margins. Size: 8 mm–10 mm. Color: Green Group 137B.
*Petiole.*—Length: 16 mm–18 mm. Color: Green Group 137B. Slight intonation of Greyed-Red Group 137A.
*Rachis.*—Several small prickles present underneath. Upper margin with stipitate glands. Color: Green Group 137A, with intonations of Greyed-Red Group 179A.
*Leaflet edge.*—Finely serrated.
*Shape.*—Leaflets are ovate.
*Leaflets.*—Number: Generally 5.
*Other.*—Matte finish. Thin texture.
Disease resistance: Average resistance to mildew and Botrytis under normal growing conditions in Half Moon Bay, Calif. and Fredensborg, Denmark.
We claim:
1. A new and distinct variety of rose plant of the miniature class, substantially as herein illustrated and described as a distinct and novel rose variety due to its abundant, dark red flowers, vigorous and compact growth, year round flowering under glasshouse conditions, suitability for production from softwood cuttings in pots, and durable flowers and foliage which make the variety suitable for distribution in the floral industry.

* * * * *

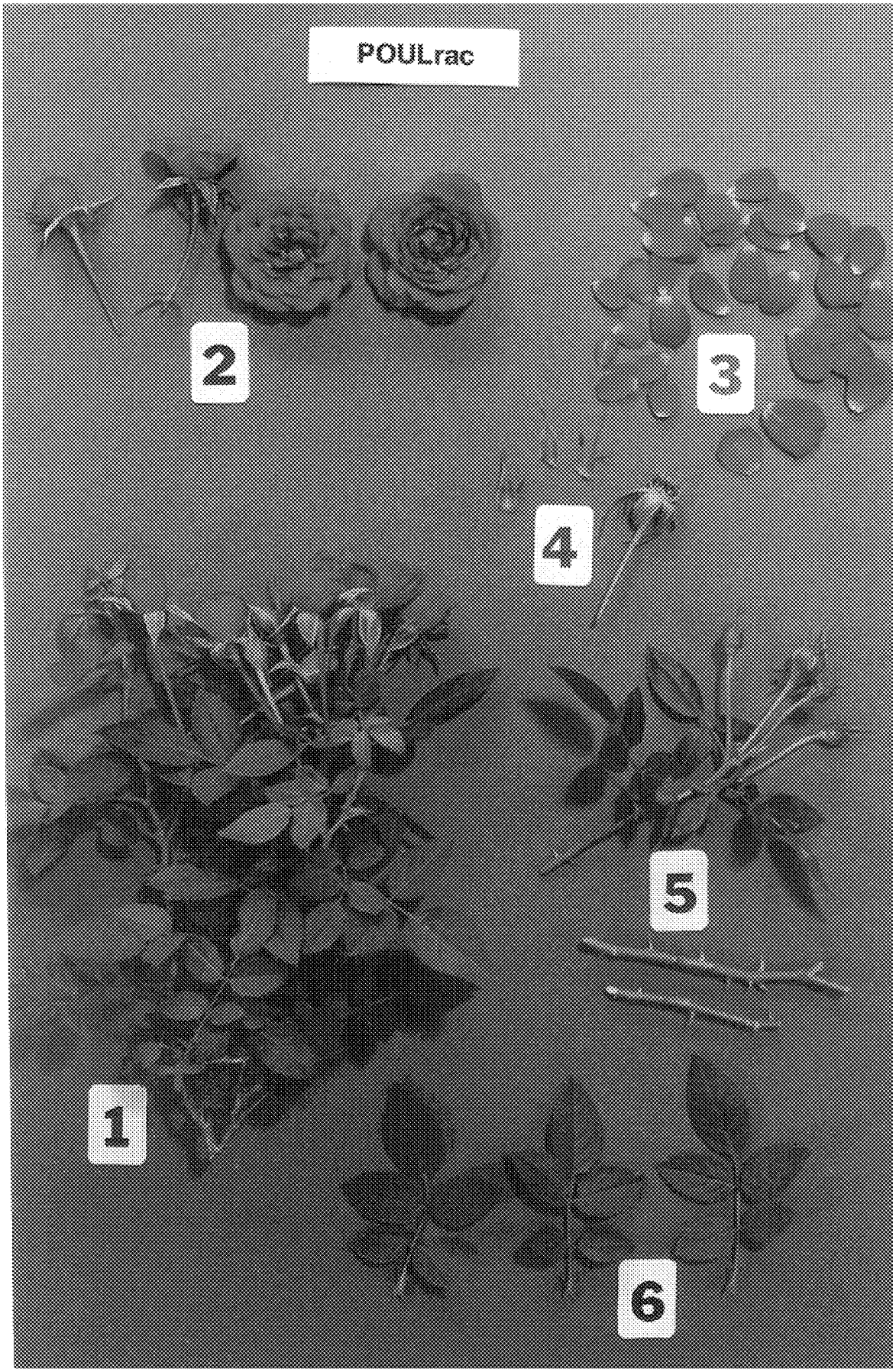
POULrac
2
3
4
5
1
6